(12) United States Patent
Powers

(10) Patent No.: US 6,438,415 B1
(45) Date of Patent: Aug. 20, 2002

(54) METHOD AND APPARATUS FOR CONTROLLING THE OPERATION AND FUNCTIONALITY OF AN ELECTROTHERAPY DEVICE

(76) Inventor: Daniel J Powers, 2145 Squak Mountain Loop SW, Issaquah, WA (US) 98027

(*) Notice: Subject to any disclaimer, the term of this patent is extended or adjusted under 35 U.S.C. 154(b) by 0 days.

(21) Appl. No.: 09/411,348

(22) Filed: Oct. 1, 1999

(51) Int. Cl.[7] ................................................. A61B 1/02
(52) U.S. Cl. ................................................. 607/2; 607/5
(58) Field of Search ............................... 607/1, 2, 4, 5, 607/9, 10, 36, 72

(56) References Cited

U.S. PATENT DOCUMENTS

| | | | |
|---|---|---|---|
| 4,097,113 A | * | 6/1978 | McKelvy ........................ 607/5 |
| 4,590,943 A | | 5/1986 | Paull et al. |
| 4,610,254 A | * | 9/1986 | Morgan et al. ................. 607/6 |
| 5,470,343 A | | 11/1995 | Fincke et al. |
| 5,471,305 A | | 11/1995 | Yoneda et al. |
| 5,607,454 A | | 3/1997 | Cameron et al. |
| 5,658,316 A | * | 8/1997 | Lamond et al. ................ 607/5 |
| 5,735,879 A | | 4/1998 | Gliner et al. |
| 5,836,993 A | | 11/1998 | Cole |
| 5,868,794 A | | 2/1999 | Barkley et al. |
| 5,879,374 A | | 3/1999 | Powers et al. |
| 6,223,077 B1 | * | 4/2001 | Schweizer et al. ............. 607/5 |

OTHER PUBLICATIONS

Cummins, et al., "Improving Survival from Sudden Cardiac Arrest: The 'Chain of Survival' Concept" *Circulation* 83: 1832–1847 (1991).
Newman, et al., "The Critical Moment, Early Defibrillation Making Waves Across America", JEMs supplement, S3–S8 Jan. (1997).

* cited by examiner

Primary Examiner—George R. Evanisko

(57) ABSTRACT

A control system for an electrotherapy device is provided. In particular, controlling the operation characteristics and functionality of an external electrotherapy device using a removable battery pack. Electrotherapy devices include defibrillator, cardioverters and training devices that simulate the operation of an electrotherapy device. Defibrillators include automatic or semi-automatic external defibrillators (AEDs). The operation characteristics include, training, administrative, automated use, manual use, and manufacturing use operation modes.

8 Claims, 5 Drawing Sheets

METHOD AND APPARATUS FOR CONTROLLING THE OPERATION AND FUNCTIONALITY OF AN ELECTROTHERAPY DEVICE

BACKGROUND OF THE INVENTION

1. Field of the Invention

This invention relates generally to a control system for an electrotherapy device. In particular, this invention relates to controlling the operation characteristics and functionality of an external electrotherapy device using a removable battery pack. Electrotherapy devices include defibrillator, cardioverters and training devices that simulate the operation of an electrotherapy device. Defibrillators include automatic or semi-automatic external defibrillators (AEDs).

2. Description of the Prior Art

Electrotherapy devices are used to provide electric shocks to treat patients for a variety of heart arrhythmias. For example, external defibrillators typically provide relatively high-energy shocks to a patient (as compared to implantable defibrillators), usually through electrodes attached to the patient's torso. External defibrillators are used to convert ventricular fibrillation or shockable tachycardia to a normal sinus rhythm. Similarly, external cardioverters can be used to provide paced shocks to convert atrial fibrillation to a more normal heart rhythm.

In 1991 the Advanced Cardiac Life Support Subcommittee of the American Heart Associate made a report to Health Professionals calling for increased access to defibrillation in order to improve the survival rates from sudden cardiac arrest (SCA). [Cummins, et al. "Improving Survival From Sudden Cardiac Arrest: The 'Chain of Survival' Concept" Circulation 83(5): 1832–1847 (1991).] The statistics themselves are staggering. On average 1000 adults die from SCA each day. Over 70% of these deaths occur in the home. Because the survival rate decreases 10% for every minute that passes, unless a defibrillator is available within the first few critical minutes, a victim of SCA has little chance of survival. If defibrillation were available, many of these people would survive. Following the AHA's recommendations, there has been increased awareness of the importance of public access defibrillation and defibrillators have become increasingly available. [See, e.g., Newman, "Early Defibrillation—Making Waves Across America," JEMS Suppl. S4–S8 (January 1997).] The first phase of early defibrillation has been training designated lay responders in proper deployment of a defibrillator. Designated lay responders include, for example, fire fighters, police officers, flight attendants and security guards. However, with 70% of SCA occurring in the home, it becomes increasingly important to design a device that can be deployed by the average citizen in a home emergency.

One problem that arises using currently available defibrillators is that, from time to time, it may be necessary to change the operation characteristics of the electrotherapy device. This change may be made either temporarily or permanently. Currently the procedures for changing operational status are cumbersome.

For example, the Laerdal Heartstart 3000 external defibrillator may be operated in either semi-automatic mode or manual mode. The operation mode of the Heartstart 3000 defibrillator may be changed from semi-automatic treatment mode to manual treatment mode by inserting a solid state memory module into a port in the defibrillator. The memory module also records information about the defibrillator's operation and segments of the patient's ECG related to defibrillator use.

As another example, the Marquette Responder 1500 external defibrillator uses a custom set-up card to set system defaults and to program the operation of the defibrillator. To use, the set-up card is inserted into a card slot in the Responder 1500 defibrillator housing. This same card slot is also used for receiving a patient data card to record patient data during a treatment operation of the defibrillator.

Finally, the Heartstream ForeRunner® uses a series of programmable/removable data cards to change the operation of the defibrillator to set-up, training or use. Details of the operation of the ForeRunner are described in U.S. Pat. No. 5,836,993 to Cole entitled "Electrotherapy Device Control System and Method," the specification of which is incorporated herein. One disadvantage to this system is that one battery type is used for all use modes, thus extended training becomes expensive.

While these solutions do allow for the operation of the device to be changed, the change of operation is not seamless and. Another disadvantage to currently available defibrillators is that there is no way for a user to upgrade the characteristics of the defibrillator without purchasing a whole new defibrillator.

Due to the portable nature of AEDs, battery packs are typically used to power the device. [See, e.g., U.S. Pat. No. 4,590,943 by Paull et al. for "System for Providing Power to Portable Defibrillator;" U.S. No. Pat. 5,471,305 by Vincent et al. for "Keyed Self-Latching Battery Pack for a Portable Defibrillator;" and U.S. Pat. No. 5,470,343 to Fincke et al. for "Detachable Power Supply for Supplying External Power to a Portable Defibrillator."] Additional features of the battery pack include, for example, the ability to detect when the battery is about to be disengaged (See U.S. Pat No. 5,868,794 by Barkley et al. for "AED and Battery Pack with Anticipatory Battery Disengagement Detection"). The SurvivaLink AED battery also include a memory chip that tracks, for example, the battery type, original installation date, maximum capacity, charges completed, minutes of operation, days of standby operation, remaining capacity and temperature. Appropriate memory chips are available from Dallas Semiconductor (www.dalsemi.com). Suitable memory chips include, for example, DS2434 through DS2438. Because of the ease of replacing the power supply, the power supply could provide a convenient way to change the operation of the defibrillator or to add features.

What is needed is a method and apparatus for controlling the operation and functionality of a defibrillator. More specifically, what is needed is a removable power source that changes the operational characteristics of the defibrillator, or provides additional functionality.

SUMMARY OF THE INVENTION

An electrotherapy device system comprising: an electrotherapy device housing; electronic circuitry disposed within the housing for delivering a therapeutic pulse to a patient; a controller disposed within the housing for determining which operation instructions to execute from ROM; a system memory communicating with the controller; a removable power supply, wherein the removable power supply has an operation memory module which communicates with the controller to control the operation mode of the electrotherapy device. Operation instructions may be stored on the system memory or the operation memory module. Additionally, operation memory module may identify the power supply type to the controller and based on that identification the controller then retrieves operation instructions from ROM. In another embodiment, operation memory module may contain ROM instructions for operating the defibrillator and wherein the controller then retrieves operation instructions from the power supply ROM. In each of these embodiments, the use type is training, administrative, automated use, manual use, or manufacturing use. Alternatively, operation memory module identifies a use type and the controller retrieves operation instructions from ROM based on the use type. The removable power supply also contains a functional module which communicates with the controller to provide additional functionality to the device. The functional module may provide additional functionality such as: RS232, fax, or modem functionality.

An electrotherapy device system comprising: an electrotherapy device housing; electronic circuitry disposed within the housing for delivering a therapeutic pulse to a patient; a controller disposed within the housing for determining which operation instructions to execute from ROM; a removable power supply, wherein the removable power supply has a functional module which communicates with the controller to provide additional functionality to the device. Similar to the embodiment above, the functional module may provide the following additional functionality: RS232, fax, modem functionality, and patient monitoring functionality. The removable power supply may also have an operation memory module which communicates with the controller to control the operation mode of the electrotherapy device. The operation instructions may alternatively be stored on the system memory or the operation memory module. In that case, the controller retrieves operation instructions from ROM based on the power supply type. Use types include: training, set-up, automated use, manual use, and manufacturing use. The operation memory module may identify a use type and the controller retrieves operation instructions from ROM based on the use type.

A method of operating an electrotherapy device system comprising: powering up an electrotherapy device; determining which operation mode is identified by a module within the battery housing; retrieving operating instructions based on the identified operation mode; and beginning electrotherapy device operation based on the retrieved instructions. Prior to powering up an electrotherapy device, a battery is installed. The identified operation mode could be training, administrative, automated use, manual use or manufacturing. The determining step includes retrieving operating instructions from the operation memory module. Alternatively, the determining step includes retrieving an identifier from the operation memory module. In this case, the identifier is an identifier that corresponds to the battery type and further wherein operating instructions retrieved are retrieved based on the identified battery type. Alternatively, the identifier is an identifier that corresponds to a use mode and further wherein the operating instructions retrieved are retrieved based on the use mode identified. An additional step of identifying additional functionality contained on the battery may also be provided.

A battery for use with a defibrillator, wherein the battery identifies an operational use mode of the defibrillator. In one embodiment, an operation memory module is associate with the battery. The operation memory module contains ROM associated with operation of the defibrillator.

A battery for use with a defibrillator wherein battery chemistry determines the use mode of the defibrillator.

DESCRIPTION OF THE PREFERRED EMBODIMENTS

The following discussion is presented to enable a person skilled in the art to make and use the invention. Various modifications to the preferred embodiment will be readily apparent to those skilled in the art, and the generic principles herein may be applied to other embodiments and applications without departing from the spirit and scope of the present invention as defined by the appended claims. Thus, the present invention is not intended to be limited to the embodiment show, but is to be accorded the widest scope consistent with the principles and features disclosed herein.

Figure 1:
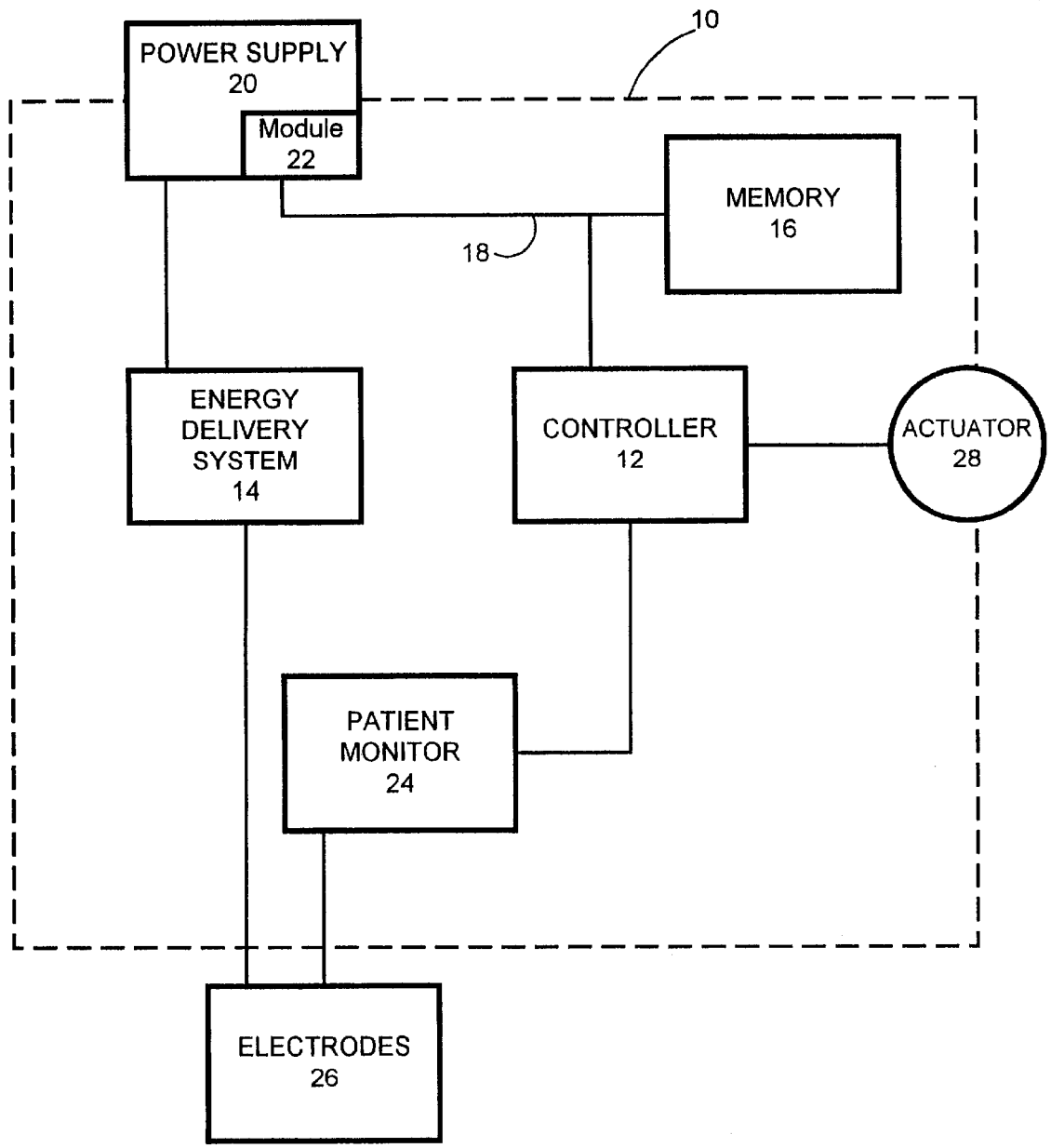
FIG. 1 is a block diagram of an electrotherapy device showing a detachable power supply containing a module according to one embodiment of this invention.

FIG. 1 is a block diagram showing a device 10. Device 10 is an electrotherapy device. The device 10 may be include the ability to defibrillate, cardiovert, or pace a patient, or a combination of these features. Device 10 has a controller 12 that operates an energy delivery system 14 and performs other aspects of the operation of the device using software instructions contained in memory 16. It should be understood that, in this and other embodiments described below, "controller" means a microprocessor, controller, gate array, other control logic, or any combination of these elements.

Controller 12 communicates with a first memory 16 via a memory bus 18. Device 10 also has a module 22 communicable with bus 18. Module 22 is attached to device 10 via power supply 20, as shown in FIG. 1. As contemplated by this embodiment, module 22 is integral with the power supply 20 and power supply 20 is removably connected to the device 10. However, module 22 need not be integral with the power supply 22. A suitable power supply would be, for example, a Li ion battery. Once the power supply 20 is attached to the device 10, module 22 may communicate with controller 12 over memory bus 18.

Electrodes 26 communicate with a patient monitor 24. In an AED, the patient monitor monitors the patient for a heart rhythm and subsequently determines whether the monitored rhythm is shockable. The patient monitor 24 communicates a shock decision to the controller 12. The controller 12, then communicates to the energy delivery system 14. The energy delivery system 14, then delivers a therapeutic energy pulse to the patient (not shown) via electrodes 26, using the power supply 20 as the energy source.

Turning to FIG. 2, power supply 20 comprises a housing 40 which features a connector 42 for connecting the power supply 20 to device 10. An energy source 44 is provided within housing 40 to power the device. Suitable energy sources are, for example, $LiMnO_2$, $LiSO_2$, Alkaline $MnO_2$, NiCAD, NiMH, Li ion, lead acid, or Li polymer. The actual configuration of the battery cells is not disclosed in order to avoid obscuring the invention. However, suitable configurations are known by those skilled in the art. Suitable configurations include, for example, the configuration described by Cameron et al. in U.S. Pat. No. 5,483,165 for "Battery System and Method for Determining a Battery Condition."

Figure 2A:
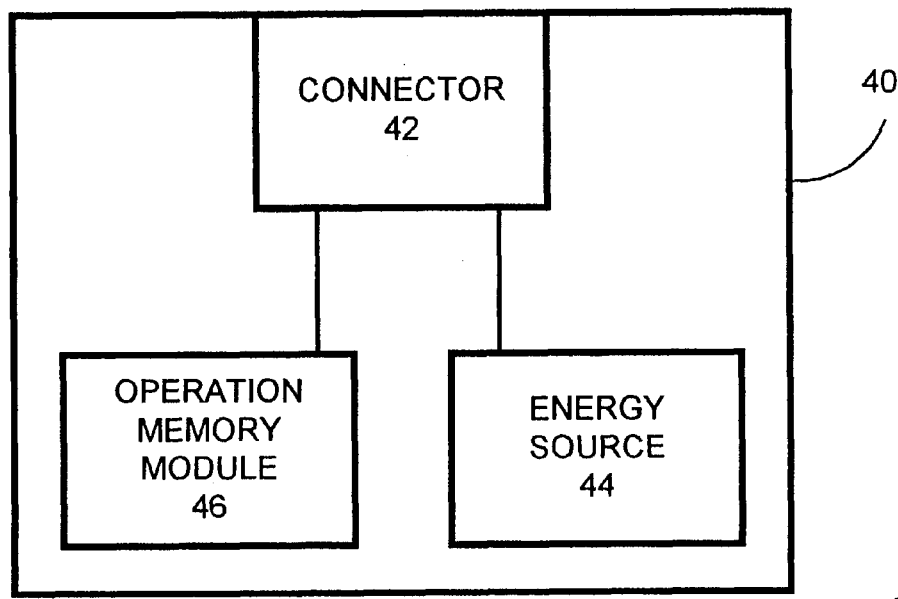
FIGS. 2A and 2B are block diagrams showing the detachable power supply of FIG. 1 wherein the module is either an operation memory module or a functional module.

Turning more specifically to the embodiment shown in FIG. 2A, an operation module 46 is provided.

In one embodiment of the invention, operation module 46 is a memory device that contains read only memory (ROM) instructions for the defibrillator operation. Thus, for example, operation module 46 contains ROM instructions pertaining to defibrillator operation as a trainer, in an administrative mode, or in use mode. The administrative mode includes, for example, set-up, self-test, and diagnostic modes. The use modes include, for example, operating in an automated mode or a manual mode.

In an alternative embodiment, operation module 46 is a memory device that contains activation ROM which activates the controller's 12 ROM operation memory stored in device memory 16. The activation ROM could, for example, be in the form of a software macro or key.

Alternatively, the activation ROM could be a value stored on a chip which identifies the desired defibrillator operation to the controller 12. Appropriate customizable memory chips are available from Dallas Semiconductor (www.dalsemi.com). Suitable memory chips include, for example, DS2434 through DS 2438. Thus, memory 46 acts as a key which enables a specific operating sequences in memory 16 to be accepted by the controller 12.

In a specific example, a DS2434 chip is set up so that a byte of the lockable nvRAM is coded to identify the battery type, where nvRAM is non-volatile random-access memory. The battery type is identified by the controller to correspond to a specific type of operation. As a result of determining that a particular battery type is inserted, the controller 12 controls the portion of operation ROM that is activated. Thus, for example, when the controller 12 identifies the battery type as $Li^+$, the controller activates software instructions for operating the defibrillator in use mode.

In yet another example, the battery housing 40 could be configured such that when the housing 40 is mechanically connected to the defibrillator 10 the operation module 22 mechanically interacts with the defibrillator to identify the battery type to the defibrillator. Thus, when a particular interaction is accomplished, operational ROM is activated in a specific sequence. Such a configuration might be accomplished with the use of pins or flanges.

In a preferred embodiment, each use mode is associated with a battery technology. Thus enabling the user to maximize cost effectiveness of a battery type with the characteristics required for a specific use. For example, a low use AED is most appropriately powered by a low maintenance, high reliability primary (non-rechargeable) power source (such as $LiMNO_2$). However, in training mode it is more desirable to provide a battery with a lost cost/hour of operation. Thus in the training scenario a rechargeable battery (such as NiMH) is appropriate. Lastly, an advanced user may require a highly reliable rechargeable solution (such as LiIon) because of frequency of use. By coupling the battery technology with the use mode, battery solutions can be optimized with still providing key functions to maximize the use modes.

Figure 2B:
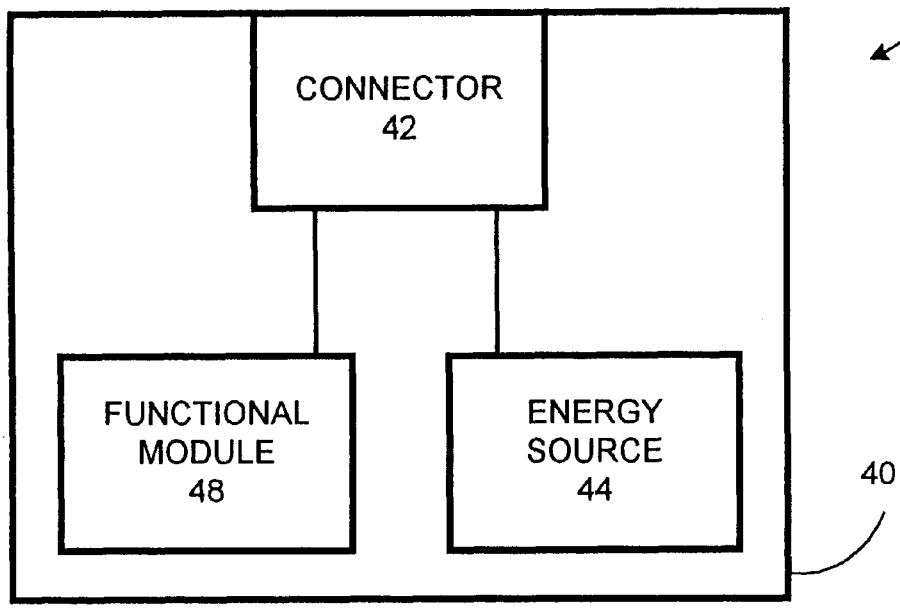

Turning to the specific example of FIG. 2B, functional module 48 is provided. Functional module 48 provides a source of removable functionality to the defibrillator. For example, additional communication ability could be provided to the defibrillator via functional module 48. Such additional functionality is, for example, RS232 capability, and fax/modem capability. Additional functionality could also include patient monitoring parameters such as $SPO_2$, $CO_2$, or 3/5 ECG lead. Importantly functional module 48 will, as appropriate, include an external interface. For example, where the additional functionality includes an $SPO_2$ monitor, an external interface in the battery housing would enable the functional module 48 to receive $SPO_2$ data from the patient.

Although not shown, as will be appreciated by those of skill in the art, housing 40 could be configured to contain both the operation memory module 46 and the functional module 48.

Figure 3:
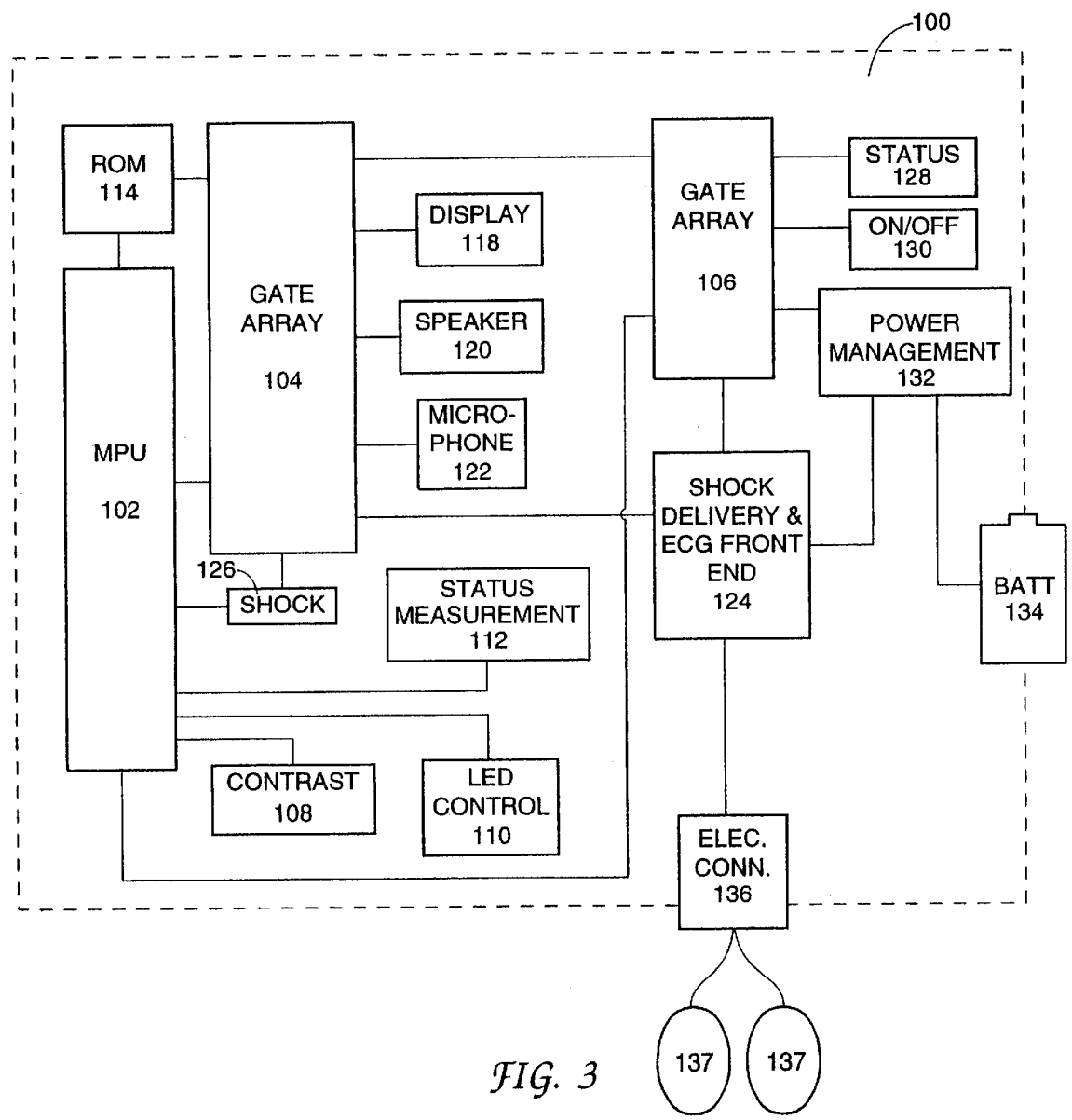
FIG. 3 shows the major components of a semi-automatic external defibrillator in block diagram form.

The major components of an AED are shown in FIG. 3 in block diagram form. Further detailed information about the operation of an AED can be obtained in U.S. Pat. No. 5,836,993, to Cole for "Electrotherapy Device Control System and Method," the specification of which is incorporated herein. As will be appreciated by those of skill in the art, the invention can be used in a variety of AEDs and is not limited to this configuration, which is used for illustration purposes only.

In this illustration, defibrillator control functions are divided among a microprocessor unit (MPU) 102 and two custom gate arrays 104 and 106.

MPU 102 performs program steps according to software instructions rovided to it from ROM 114. MPU 102 controls the operation of certain buttons such as display contrast buttons 108) and certain system LED's 110 (such as LED's associated with the shock button and the electrode connector). MPU 102 also receives system status information as shown by block 112.

Gate array 104 implements the memory map to system ROM 114. System ROM 114 is preferably flash ROM, although EPROM or any other electrically erasable and programmable nonvolatile memory could be used. Gate array 104 also controls a display 118, a speaker 120, and a microphone 122. Gate array 104 can actuate a relay within the shock delivery and ECG front end system 124 in response to actuation of a shock button 126 by a user during treatment mode.

Gate array 106 provides a system monitor function by performing automatic self-tests of the defibrillator and its components. The gate array 106 displays the operational status of the defibrillator on a status display 128. Details of suitable self-tests may be found in U.S. Pat, No. 5,879,374, to Powers, et al. for "External Defibrillator with Automated Self-Testing Prior to Use," the specification of which is incorporated herein by reference. Gate array 106 is also the defibrillator's interface with a user-activated on/off switch 130. Gate array 106 controls the power management subsystem 132 to provide power to operate system components from power supply 134 and to provide energy to the shock delivery system's capacitor(s) for a therapeutic shock during treatment mode. Gate array 106 also interfaces with the defibrillator's ECG front end, enables the shock delivery system to deliver a shock in response to detection of a patient ECG pattern requiring treatment (and actuation of the shock button), and controls delivery of the shock to electrode connector 136 in response to shock delivery status information obtained during delivery of the shock. Further information regarding this last function may be found in U.S. Pat. No. 5,735,879 to Gliner et al. for "Electrotherapy Method for External Defibrillators," and U.S. Pat. No. 5,607,454, to Cameron et al. for "Electrotherapy Method and Apparatus," the specifications of which are incorporated herein.

These defibrillator components communicate with each other over suitable communication buses, as shown.

External defibrillator 100 can be operated in different modes, such as selftest mode, stand-by mode, set-up mode, patient treatment mode, training mode and code-transfer mode. The operational characteristics of defibrillator 100 differ in each mode. In addition, the operational characteristics of the defibrillator in any one of the modes can be changed as explained below.

Operation of the external defibrillator of this embodiment commences with the insertion of a power supply 134. Once gate array 106 determines that a power supply 134 has been inserted to provide power to the defibrillator, gate array 104 prompts MPU 102 to begin its boot sequence. The boot sequence begins with MPU 102 sending out a series of addresses to power supply 134. Where the power supply 134 includes an operation memory module 46 (shown in FIG. 2A), the MPU 102 determines the identity of the power supply 134 from the memory module 46. In one embodiment, MPU 102 processes a boot series from ROM 114 that corresponds to the power supply 134 identity. Where, the power supply 134 contains a functional module 48, the MPU 102 identifies the additional functionality that is available as a result of the presence of the power supply 134 and proceeds to process a boot series and operation mode that accounts for the presence of additional functionality.

Where the power supply 134 identifies itself as a power supply 134 corresponding to "use mode," the defibrillator's initial operation mode when booting from system ROM 114 may nonetheless be a self-test mode during which the defibrillator performs an array of self-tests responding to insertion of the battery and possibly to the passage of time or an environmental event. Successful performance of these self-tests then place the AED in stand-by mode. Stand-by mode is the precursor to patient treatment mode, wherein the AED delivers therapy to a patient. Stand-by mode and treatment mode are components of use mode.

As is known in the art, while in patient treatment mode, the defibrillator 100 typically (1) determines whether electrodes 137 are attached to electrode connector 136; (2) receives ECG information from a patient through such electrodes; (3) analyzes the ECG information to determine whether a therapeutic shock is advised; and (4) delivers a shock to the patient through the electrodes 137 if a shock is advised and if the shock button 126 is actuated by a user.

Manufacturing use enables specialized manufacturing routines to be performed on the defibrillator in the process of manufacturing the device.

The operational characteristics of defibrillator 100 can be controlled by operation memory module 46 of the power supply 134 in several ways. In one embodiment, MPU 102 can be operated using instructions obtained solely from the operation memory module 46 without using instructions from system ROM 114. After the boot sequence responding to power supply insertion, the instructions in system ROM 114 instruct MPU 102 to read instructions from the operation memory module 46. Where the operation memory module 46 contains executable code or instructions, MPU 102 ceases receiving instructions from system ROM 114 and begins executing instructions taken from the operation memory module 46.

Figure 4A:
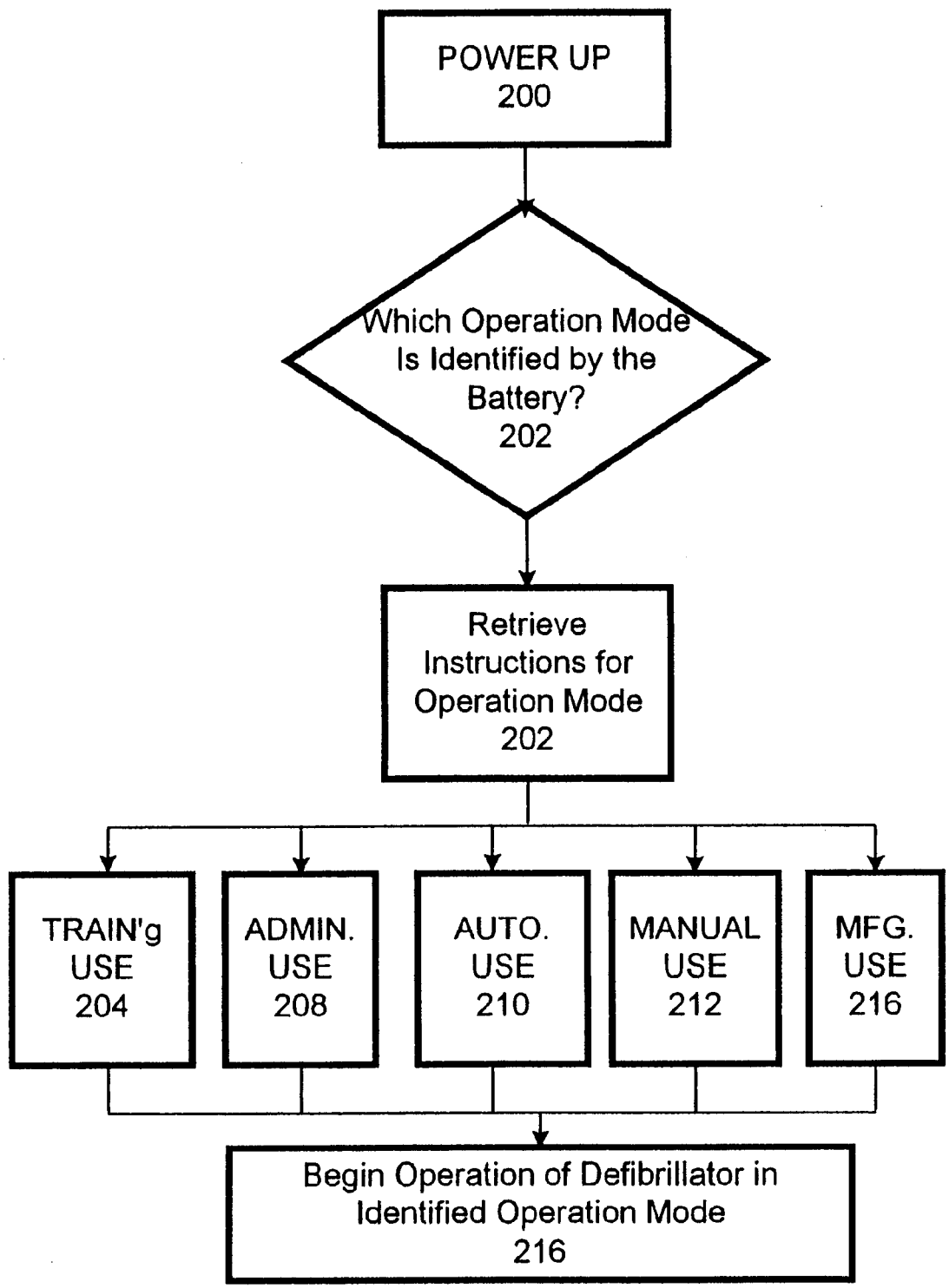
FIGS. 4A and 4B are flow charts showing methods of operating the electrotherapy device according to the invention.

Turning to FIG. 4A, the method of operating a defibrillator when the battery includes an operation memory module 46 is shown. Initially, the defibrillator is powered up 200. After powering the defibrillator, the MPU determines which operation mode is identified by the battery 202. Depending on which mode is identified in 202, the defibrillator will retrieve instructions for the corresponding operation mode 204: training 206, administrative 208, automated use 210, manual use 212, or manufacturing use 214 modes. Thereafter the defibrillator will begin operation in the selected operation mode 216.

Figure 4B:
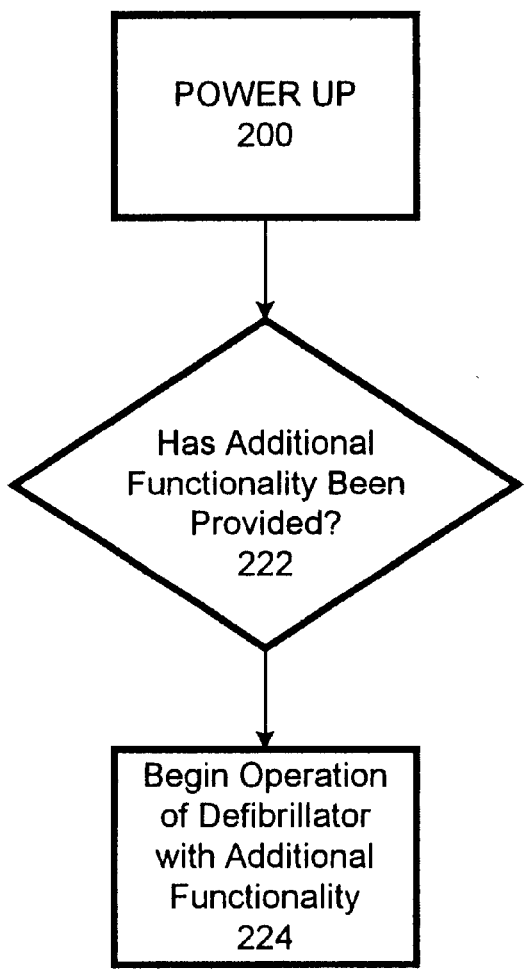

Turning now to FIG. 4B, the method of operating a defibrillator when the battery includes a functional module 48 is shown. Initially, the defibrillator is powered up 200. After powering the defibrillator, the MPU determines which whether additional functionality is provided 222. Depending on the functionality that is provided 222, the defibrillator will retrieve instructions to modify its operation to account for the additional functionality. Thereafter the defibrillator will begin operation 224 with communication with the additional functionality enabled.

Of course, if the battery includes both the operational memory module 46 and the functional module 48, the operation of the defibrillator would combine the steps shown in FIGS. 4A and 4B.

As discussed above, other modifications falling within the scope of this invention will be apparent to persons of skill in the art. Thus, the invention is not to be limited by the specification, but interpreted according to claims that follow.

What is claimed is:

1. An electrotherapy system comprising:
   an electrotherapy device housing;
   electronic circuitry disposed within the housing for delivering a therapeutic pulse to a patient;
   a controller disposed within the housing;
   a system memory communicating with the controller; and
   a removable power supply comprising an operation module storing information that identifies a set of initialization operations to the controller,
   wherein the operation module comprises a memory storing instructions for operating the system in a particular operational mode.

2. The electrotherapy system of claim 1, wherein:
   a set of operation instructions corresponding to the operation module are stored within one from the group of the system memory and the operation module.

3. The Electrotherapy system of claim 1, wherein:
   the operation module identifies a use type and the controller retrieves instructions from the system memory in accordance with the use type.

4. An electrotherapy system comprising:
   an electrotherapy device housing;
   electronic circuitry disposed within the housing for delivering a therapeutic pulse to a patient;
   a controller disposed within the housing;
   a system memory communicating with the controller; and
   a removable power supply comprising an operation module storing information that identifies a set of initialization operations to the controller,
   wherein the operation module comprises a memory storing instructions for operating the system in one from the group of a training, an administrative, an automated, a manual, and a manufacturing mode.

5. The electrotherapy system of claim 4, wherein:
   the removable power supply is characterized by a power supply type, and the operation module identifies a power supply type to the controller.

6. The Electrotherapy system of claim 3, wherein:
   the operation module identifies one from the group of a training, a set-up, an automated, a manual, and a manufacturing use type, and the controller retrieve instructions from the system memory in accordance with the use type identified by the operation module.

7. An electrotherapy system comprising:

an electrotherapy device housing; electronic circuitry disposed within the housing for delivering a therapeutic pulse to a patient;

a controller disposed within the housing;

a system memory communicating with the controller; and a removable power supply comprising an operation module storing information that identifies a set of initialization operations to the controller, wherein the removable power supply further comprises a functional module that communicates with the controller to support a type of functionality associated with the functional module.

8. The Electrotherapy system of claim 7, wherein: the functional module also provides one from the group of an external communication function and a patient monitoring function to the system.

* * * * *